(12) United States Patent
O'Day

(10) Patent No.: US 9,352,117 B2
(45) Date of Patent: May 31, 2016

(54) INFUSION CATHETER AND METHODS

(75) Inventor: Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 625 days.

(21) Appl. No.: 13/814,339

(22) PCT Filed: Sep. 26, 2011

(86) PCT No.: PCT/US2011/053223
§ 371 (c)(1),
(2), (4) Date: Feb. 5, 2013

(87) PCT Pub. No.: WO2012/047577
PCT Pub. Date: Apr. 12, 2012

(65) Prior Publication Data
US 2013/0138077 A1    May 30, 2013

Related U.S. Application Data

(60) Provisional application No. 61/389,937, filed on Oct. 5, 2010.

(51) Int. Cl.
*A61M 25/00* (2006.01)
*B26F 1/00* (2006.01)

(52) U.S. Cl.
CPC .......... *A61M 25/0013* (2013.01); *A61M 25/007* (2013.01); *A61M 25/0015* (2013.01); *A61M 25/0023* (2013.01); *B26F 1/0015* (2013.01); *A61M 25/0075* (2013.01); *Y10T 83/0237* (2015.04)

(58) Field of Classification Search
CPC ..................... A61M 25/0015; A61M 25/0013; A61M 25/0023; A61M 25/007; A61M 25/0075; B26F 1/0015; Y10T 83/023
See application file for complete search history.

(56) References Cited

U.S. PATENT DOCUMENTS

| | | | |
|---|---|---|---|
| 3,888,249 A | 6/1975 | Spencer | |
| 4,737,152 A | 4/1988 | Alchas | |
| 4,973,319 A | 11/1990 | Melsky | |
| 4,995,863 A | 2/1991 | Nichols et al. | |
| 5,030,210 A | 7/1991 | Alchas | |

(Continued)

FOREIGN PATENT DOCUMENTS

| | | |
|---|---|---|
| EP | 0381062 | 8/1990 |
| FR | 2940914 | 1/2013 |

(Continued)

*Primary Examiner* — Rebecca E Eisenberg
(74) *Attorney, Agent, or Firm* — Liell & McNeil

(57) ABSTRACT

An infusion catheter includes an elongate catheter body having a longitudinally extending fluid supply passage, and a plurality of stellate side ports for infusing a treatment fluid from the fluid supply passage into a body lumen of a passage. Each of the stellate side ports is defined by sets of at least three convergent leaves having an attached basal edge, a terminal tip, and first and second free edges extending between the attached basal edge and the terminal tip. Making an infusion catheter includes forming a plurality of stellate side ports in fluid communication with a fluid supply passage of an elongate catheter body, each of the stellate side ports being defined by a set of at least three convergent leaves, and setting an infusion length of the infusion catheter during the forming step via spacing the stellate side ports between proximal and distal ends of the elongate catheter body.

21 Claims, 5 Drawing Sheets

(56) References Cited

U.S. PATENT DOCUMENTS

| | | |
|---|---|---|
| 5,085,635 A | 2/1992 | Cragg |
| 5,160,325 A | 11/1992 | Nichols et al. |
| 5,250,034 A | 10/1993 | Appling et al. |
| 5,267,979 A | 12/1993 | Appling et al. |
| 5,460,618 A | 10/1995 | Harreld |
| 5,522,807 A | 6/1996 | Luther |
| 5,531,679 A | 7/1996 | Schulman et al. |
| 5,573,509 A | 11/1996 | Thornton |
| 5,776,096 A | 7/1998 | Fields |
| 6,027,487 A | 2/2000 | Crocker |
| 6,063,069 A | 5/2000 | Cragg et al. |
| 6,293,958 B1 * | 9/2001 | Berry et al. .................. 606/191 |
| 6,350,253 B1 * | 2/2002 | Deniega et al. .......... 604/164.02 |
| 6,524,300 B2 | 2/2003 | Meglin |
| 6,635,027 B1 | 10/2003 | Cragg et al. |
| 6,723,075 B2 | 4/2004 | Davey et al. |
| 2003/0032937 A1 | 2/2003 | Griego et al. |
| 2008/0200788 A1 | 8/2008 | Brister et al. |
| 2009/0054825 A1 | 2/2009 | Melsheimer et al. |

FOREIGN PATENT DOCUMENTS

| | | |
|---|---|---|
| WO | 00/06239 | 2/2000 |
| WO | 2006/122026 | 11/2006 |

* cited by examiner

INFUSION CATHETER AND METHODS

This patent application is a U.S. National Stage of International Patent Application Ser. No. PCT/US2011/053223, filed Sep. 26, 2011, and claims the benefit of the filing date of U.S. Provisional Patent Application Ser. No. 61/389,937, filed Oct. 5, 2010.

TECHNICAL FIELD

The present disclosure relates generally to infusion mechanisms for intraluminal treatment of a patient, and relates more particularly to an infusion catheter having stellate side ports for supplying a treatment fluid into a body lumen.

BACKGROUND

Percutaneous access to the cardiovascular system is used to diagnose, evaluate, and treat a variety of conditions. A typical procedure involves passing a wire guide through an opening in a patient's skin often by way of an introducer sheath, which connects to a vascular structure such as a vein or artery. The wire guide can then be passed through the cardiovascular system to a location of interest within the patient. Once the wire guide has been appropriately positioned, a catheter may be passed into the patient and guided by the wire guide to a location where a procedure is to be performed. Angioplasty, imaging, and the placement of stents, grafts, filters and other devices, are common procedures which are performed according to variations of the above general technique. It is also common to use percutaneous access for the placement of catheters which deliver fluid at an intraluminal treatment site. Devices known as infusion catheters are used to deliver a therapeutic treatment fluid such as a thrombolytic agent to a clot or the like within a vein or artery. A wide variety of infusion catheter designs are known and commercially available. One general class of infusion catheters utilizes a longitudinally extending lumen which connects a supply of therapeutic fluid located outside of the patient with an intraluminal space by way of ports communicating between the lumen and the intraluminal space. Various locations on a patient's body may be used to percutaneously access the cardiovascular system for infusion in this manner. While in some instances a location of interest within the patient can be reached from a nearby access point, in other instances a preferred access point may be relatively farther away. As a result, relatively long infusion catheters are often used, to enable a treatment site within, for example, a patient's torso, to be reached form a relatively remote access point such as the patient's neck or ankle area. One problem with conventional infusion catheters may be a difficulty in supplying fluid uniformly along the catheter infusion length. Various strategies, such as non-uniform distribution of the infusion ports have been suggested to address this challenge, meeting with varying degrees of success. The use of multiple lumens for conveying fluid independently to different sections of a catheter infusion length has also been proposed. Such designs are believed to provide for more uniform infusion than is practicable or possible with certain single lumen designs.

Still other strategies have included the use of specialized ports for supplying the treatment fluid into a body lumen of a patient. Pressure responsive slit designs are well known, in which normally closed slits are positioned along an infusion length of an infusion catheter, and treatment fluid supplied into a lumen connecting with the pressure responsive slits. When a pressure of the treatment fluid exceeds a threshold sufficient to overcome a closing bias of the pressure responsive slits, treatment fluid can begin to flow out of the infusion catheter through the slits and into a body lumen of the patient. Such designs appear to improve over certain conventional port configurations, as the relatively mild pressurization of treatment fluid within the infusion catheter is believed to impart a tendency for fluid pressure within the catheter lumen to more or less equalize prior to commencing infusion. As a result, similar internal pressures prevail along the catheter infusion length and, hence, non-uniformity in flow rate out of the catheter is reduced. While certain of these known designs have seen commercial success, there remains room for improvement both in the practical implementation of infusion procedures and methods by which infusion catheters are made.

SUMMARY

In one aspect, an infusion catheter includes an elongate catheter body having an outer body surface, and an inner body surface defining a fluid supply passage extending longitudinally between a proximal body segment having an inlet to the fluid supply passage, and a distal body segment. The infusion catheter further includes a plurality of stellate side ports in fluid communication with the fluid supply passage and having a distribution within the distal body segment which defines a catheter infusion length. Each of the stellate side ports is defined by sets of at least three convergent leaves formed integrally with the elongate catheter body, and each of the convergent leaves having an attached basal edge, a terminal tip, and first and second free edges extending between the attached basal edge and the terminal tip.

In another aspect, a method of making an infusion catheter includes forming a plurality of stellate side ports in fluid communication with a fluid supply passage in an elongate catheter body, each of the stellate side ports being defined by a set of at least three convergent leaves. The method further includes setting an infusion length of the infusion catheter during the forming step at least in part by spacing the stellate side ports longitudinally between proximal and distal ends of the elongate catheter body.

In still another aspect, a method of supplying a treatment fluid into a body lumen of a patient includes conveying treatment fluid through a longitudinally extending fluid supply passage in an elongate catheter body of an infusion catheter. The method further includes infusing the treatment fluid from the elongate catheter body into the body lumen, and controlling an infusion flow of the treatment fluid at least in part by passing the treatment fluid through a plurality of stellate side ports fluidly connecting the fluid supply passage with the body lumen.

DETAILED DESCRIPTION

Figure 1:
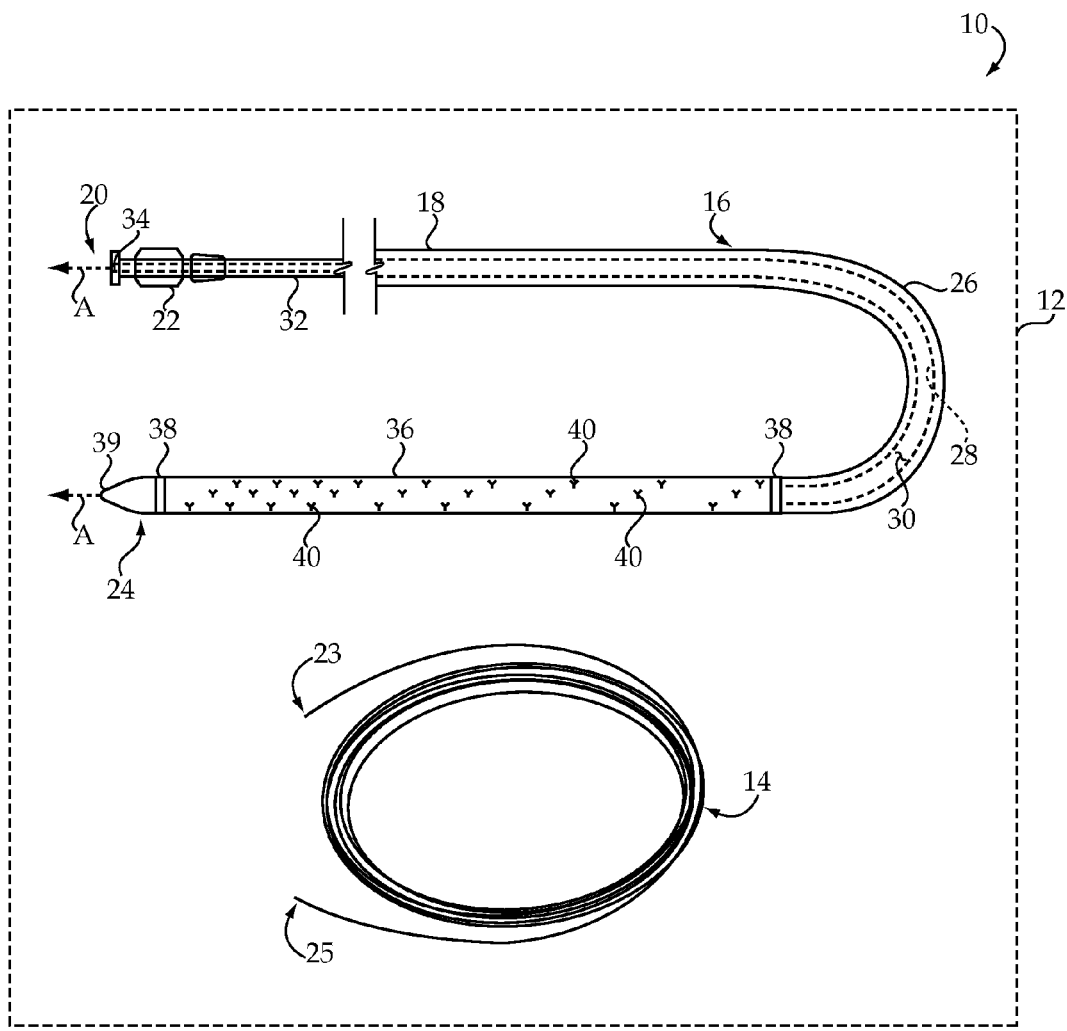
FIG. 1 is a side diagrammatic view of an intraluminal treatment system, according to one embodiment.

Referring to FIG. 1, there is shown an intraluminal treatment system 10 which may be used for treating an intraluminal site in a patient. System 10 may include an infusion catheter 16, and a wire guide 14, catheter 16 and wire guide 14 being positioned within a sterile package 12. Sterile package 12 may include a sealed, peel-open pouch in one embodiment. Other packaging and component protection features such as a tube protector coil, adapters and fittings, an introducer sheath, or still other components may be included. As will be further apparent from the following description, system 10 may be uniquely adapted to address certain challenges relating to controlling a flow of a treatment fluid into a body lumen of a patient during an infusion procedure.

Wire guide 14 may include a proximal tip 23 and a distal tip 25, and may be relatively soft or floppy in a region adjacent distal tip 25 in a manner well-known in the art. As further described herein, wire guide 80 may be used in guiding catheter 16 to a treatment site within a patient. In one embodiment, catheter 16 may be configured for passing over wire guide 80, and could be configured as a rapid exchange catheter in certain embodiments. Rather than over-the-wire placement, catheters contemplated herein might also be placed by any of a variety of other placement methods such as via the use of a placement sheath or the like. In certain embodiments (not shown), a wire guide comprising a part of system 10 might also serve functions other than guiding/placement of catheter 16, such as blocking a distal opening in catheter 16 by way of an occlusion bulb positioned adjacent a distal tip of the wire guide.

Catheter 16 may include an elongate catheter body 18 having an outer body surface 26, and an inner body surface 28 defining a fluid supply passage 30 extending longitudinally between a proximal body segment 32 having an inlet 34 to supply passage 30, and a distal body segment 36. Catheter body 18 may further include a proximal end 20 which includes a fitting or manifold 22 having inlet 34 formed therein for fluidly connecting supply passage 30 with an extraluminal supply of treatment fluid, as further described herein. Catheter body 18 may also include a distal end 24 which includes a distal tip 29 having a narrowing taper in a proximal to distal direction. Catheter body 18 further defines a longitudinal axis A extending through proximal segment 32 and distal segment 36. A plurality of stellate side ports 40 are formed in catheter body 18 and are in fluid communication with supply passage 30. Side ports 40 may include a distribution within distal body segment 36 which defines a catheter infusion length. A set of radiopaque markers 38 may be positioned at opposite ends of the catheter infusion length to assist a clinician in visualizing catheter 16 during placement and use in a conventional manner.

Figure 2:
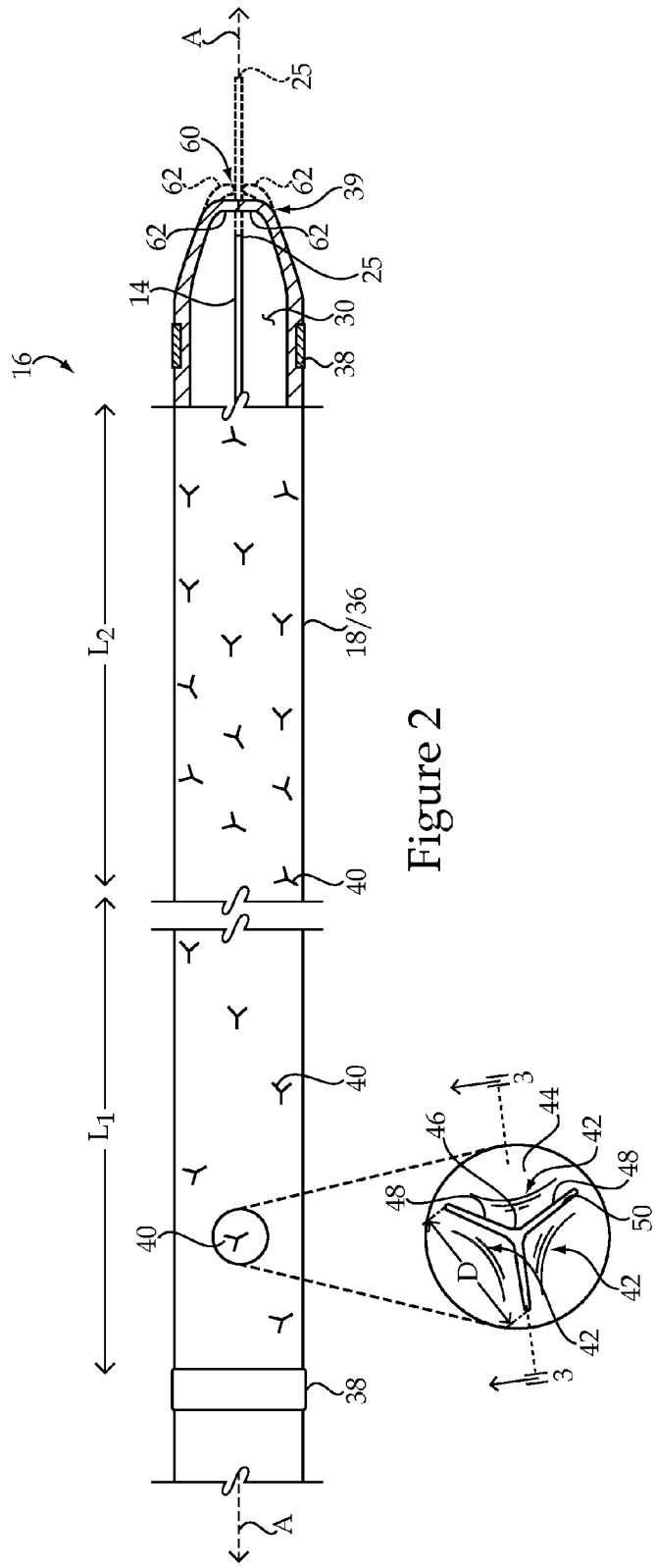
FIG. 2 is a partially sectioned side diagrammatic view, including a detailed enlargement, of a portion of an infusion catheter, according to one embodiment.

Referring also now to FIG. 2, there is shown a partially sectioned side diagrammatic view of distal body segment 36, including a detailed enlargement. In FIG. 2, wire guide 14 is shown positioned within catheter body 18, and in particular extending longitudinally through supply passage 30 to a location at which distal tip 25 of wire guide 14 is located just proximally of a gated wire guide opening 60 formed in distal tip 39. Gated wire guide opening 60 may communicate with fluid supply passage 30, and enables wire guide 14 to be advanced distally through tip 39 via deforming a plurality of flaps 62. Flaps 62 may be configured to open and close gated wire guide opening 60 in response to inserting or removing wire guide 14. In one practical implementation strategy, flaps 62 may include a total of three flaps arranged radially symmetrically about axis A, and each having a generally triangular shape. In other embodiments, a different number of flaps, or a biased closed circular port having no flaps might be used. Flaps 62 may be formed integrally with material of catheter body 18, and include a closing bias, for reasons which will be further apparent from the following description. In FIG. 2, flaps 62 are shown in solid lines as they might appear in a first configuration closing gated wire guide opening 60, and are shown in phantom as they might appear at a second configuration when wire guide 14 has been advanced through opening 60 such that distal tip 25 is positioned outside of catheter body 18 at a location distal to tip 39.

As mentioned above, a distribution of stellate side ports 40 within distal segment 36 may define a catheter infusion length. In one embodiment, stellate side ports 40 might be uniformly distributed within distal segment 36, however, in a practical implementation strategy, stellate side ports 40 may have a relatively denser distribution in a distal portion of the catheter infusion length, shown via length dimension $L_2$ in FIG. 2. In a proximal portion of the catheter infusion length, shown via length dimension $L_1$, a distribution of stellate side ports 40 may be relatively less dense. A wide variety of different patterns and numbers of stellate side ports 40 are possible. For instance, stellate side ports might be arranged in longitudinally extending rows, or radial bands circumferential of longitudinal axis A. Stellate side ports 40 might also include a random distribution pattern within distal segment 36. In one practical implementation strategy, stellate side ports 40 may be positioned in a spiraling pattern at a plurality of different radial locations and a plurality of different axial locations relative to a longitudinal center axis of supply passage 30, which is co-linear with longitudinal axis A and commonly labeled therewith, approximately as shown in FIG. 2. A number of stellate side ports 40 may be equal to 10 or greater and in certain embodiments depending at least in part on catheter infusion length, a number of stellar side ports 40 might be greater than 20, or even greater than 100.

In one example configuration, length $L_1$ is equal to about 40 cm, and $L_2$ is equal to about 10 cm, whereas a total length of catheter 16 is equal to about 130 cm, and an outer diameter of catheter body 18 is equal to about 5 French. In this example configuration, stellate side ports 40 may have a uniform longitudinal spacing and a density of about 2.5 ports per cm within length $L_1$, and a uniform longitudinal spacing and a density of about 5 ports per cm within length $L_2$. This example configuration has been demonstrated to provide acceptable flow of infusate over an entirety of the catheter infusion length. In particular, in a laboratory testing set-up a flow rate of an infusate such as saline through catheter 16, of about 125 ml per hour using a standard IV pump, resulted in an observed flow of liquid infusate from the distal 10 cm segment, $L_2$. This contrasts with certain similarly designed catheters but having conventional side port designs in which similar test conditions can be expected to result in zero or near zero flow from a distal 10 cm of the infusion length. The example configuration used stellate side ports 40 having a port geometry further described below in connection with FIGS. 2, 3 and 4.

Figure 3:
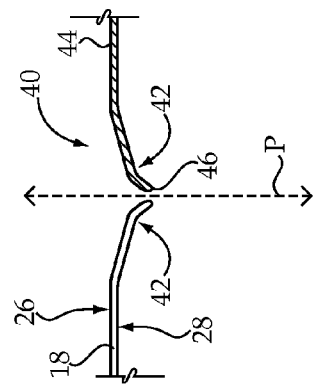
FIG. 3 is a sectioned view taken along line 3-3 of FIG. 2.

As mentioned above, FIG. 2 includes a detailed enlargement depicting features of an example one of stellate side ports 40 in some detail. Referring also to FIG. 3, there is shown a sectioned view taken along line 3-3 of FIG. 2. Each of stellate side ports 40 may be defined by a set of at least three convergent leaves 42 formed integrally with catheter body 18. As used herein, the term "formed integrally" should be understood to mean that the subject convergent leaves 42 are formed from material continuously transitioning with material of catheter body 18. In one practical implementation strategy, catheter body 18 may be made from a nylon extrusion in which passage 30 is formed during the extrusion process, but any other suitable manufacturing process, or biocompatible material such as fluoropolymer materials might be used. Each of stellate side ports 40 may define a center port axis, shown via reference letter P in FIG. 3. In one embodiment, center port axis P may be oriented normal to and intersects longitudinal axis A. Center port axis P may also be understood as a line oriented normal to longitudinal axis A and extending through a geometric center of the corresponding stellate side port 40, and intersecting longitudinal axis A.

Each of the convergent leaves 42 defining stellate side ports 40 may include an attached basal edge 44, a terminal tip 46, and first and second free edges 48 extending between the corresponding attached basal edge 44 and terminal tip 46. Each stellate side port 40 may further include slits 50 radiating outward from center port axis P, and each of convergent leaves 42 within each set may adjoin two of slits 50. Each of the convergent leaves 42 may further include a taper narrowing toward the corresponding center port axis P. In the detailed enlargement shown in FIG. 2, it may be noted that each of convergent leaves 42 defines a triangular shape in a projection plane intersecting and oriented normal to the corresponding center port axis P, i.e. a plane of the page in FIG. 2. A width dimension D located in this same plane, and extending from an imaginary line co-linear with one basal edge 44 to a second imaginary line tangent to an outer end of an oppositely positioned slit 50, may be equal to about $13/1000$ths inches. It may further be noted from FIG. 3 that each of convergent leaves 42 curves relative to outer body surface 26 such that the corresponding terminal tip 46 plunges inwardly into supply passage 30. This configuration positions terminal tips 46 such that they are incident to an outward flow of fluid from fluid supply passage 30.

Each of convergent leaves 42 may also be understood to define a non-uniform curve in a section plane which includes a plane of the corresponding center port axis P. The non-uniform curve may include a shallower incipient curve segment adjoining attached basal edge 44, and a steeper terminal segment which adjoins terminal tip 46. Thus, a curvature of each leaf 42 may increase in a direction from basal edge 44 toward terminal tip 46. The example stellate side port 40 depicted in FIGS. 2 and 3 may also be understood to be radially symmetric about the corresponding center port axis P, and axially asymmetric relative to the corresponding center port axis P. The radially symmetric and axially asymmetric configuration of the illustrated stellate side port 40 results at least in part from the manner in which it is formed during making catheter 16. In particular, a piercing angle and a piercing direction used in forming stellate side ports 40 can determine at least in part a geometry of the resulting stellate side port 40. In the example of FIGS. 2 and 3, a piercing tool has been passed in a piercing direction from an outside of catheter body 18 to an inside of catheter body 18, and at a piercing angle of about 90° relative to longitudinal axis A. As further discussed below, varying a piercing angle and/or a piercing direction may impart a different geometry to a stellate side port.

Figure 4:
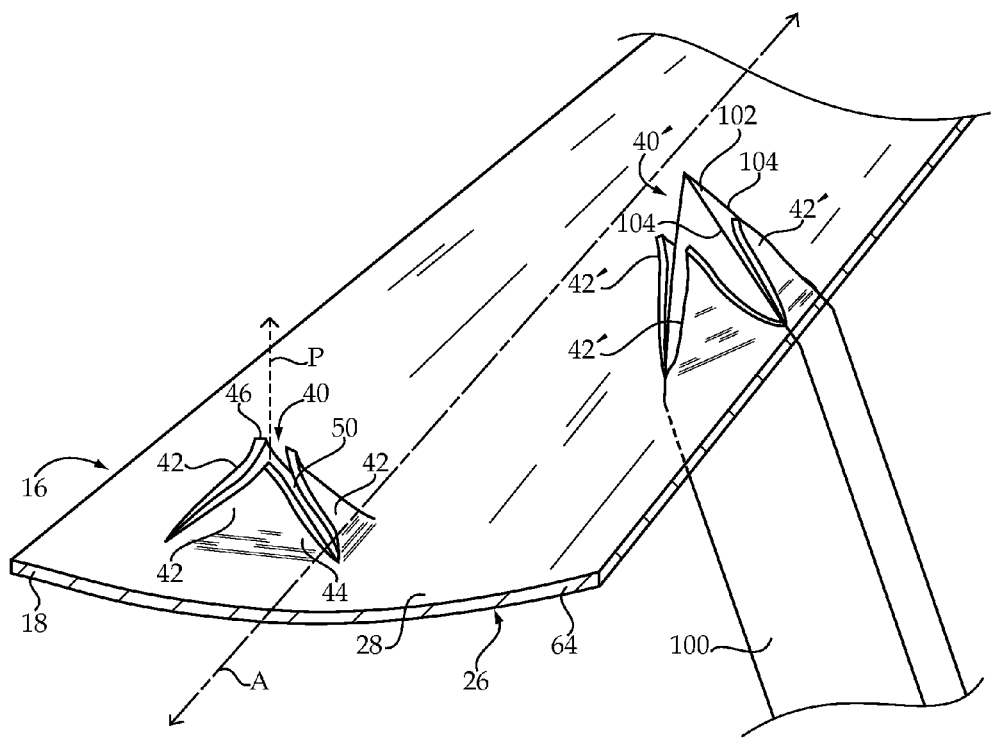
FIG. 4 is a pictorial view of a portion of an infusion catheter during forming a side port therein, according to one embodiment.

Referring to FIG. 4, there is shown a sectioned view through a portion of elongate catheter body 18 as it might appear viewed from inside passage 30 during making infusion catheter 16. A body wall 64 of catheter body 18 is shown extending between outer body surface 26 and inner body surface 28. At the stage shown in FIG. 4, a first stellate side port 40 defined by a set of three convergent leaves 42 has been formed, and a second stellate side port denoted via reference numeral 40' and also having three convergent leaves 42' is in the process of being formed. It may be noted that stellate side ports 40 and 40' are located at different radial locations about longitudinal axis A, and also at different longitudinal or axial locations. As noted above, an infusion length of catheter 16 may be defined by a distribution of stellate side ports 40, and thus a technician manually forming stellate side ports 40, or a machine, may progress longitudinally along and radially about catheter body 18 forming stellate side ports 40 at desired locations until a desired infusion length and pattern of side port arrangement has been achieved. In one practical implementation strategy, forming each of stellate side ports 40 may occur by cutting convergent leaves 42, 42' from material of catheter body 18. In particular, forming stellate side ports 40, 40' may include simultaneously cutting convergent leaves 42, 42' of each set in body wall 64 without removing material of catheter body 18.

Stellate side port 40 is shown in FIG. 4 as it might appear where a pyramidal tip 102 of a piercing tool 100 has been passed through body wall 64 and then removed. One suitable piercing tool includes an SC-11 straight trocar cutting needle commercially available from Covidien, of Mansfield, Mass. It may further be noted that piercing tool 100 has been passed through body wall 64 to a partial insertion depth of pyramidal tip 102 in forming side port 40'. In other words, pyramidal tip 102 has been passed through body wall 64 far enough that a plurality of cutting edges 104, in the illustrated case three cutting edges, have cut material of catheter body 18 to simultaneously form convergent leaves 42', but not so far that pyramidal tip 102 has passed completely through body wall 64. From the stage depicted in FIG. 4, piercing tool 100 may be withdrawn from the partial insertion depth. It has been discovered that controlling puncture depth via stopping pyramidal tip 102 at the partial insertion depth, and then withdrawing piercing tool 100 without further advancing piercing tool 100 from the partial insertion depth, results in stellate side ports having suitable geometric and functional properties, although the present disclosure is not limited in this regard. At the stage shown in FIG. 4, it may still further be noted that piercing tool 100 has been passed through body wall 64 in an outside-to-inside piercing direction, and also that a piercing angle of piercing tool 100 is approximately normal to longitudinal axis A. As alluded to above, using piercing tool 100, or another suitable piercing tool, at a different piercing angle or direction may impart a particular geometry to stellate side ports formed thereby.

To this end, the completed stellate side port 40 shown in FIG. 4 is shaped such that the attached basal edges 44 of the associated convergent leaves 42 each define one edge of a pyramidal polyhedron. Each of the adjoining slits 50 defines one edge of the corresponding pyramidal polyhedron. In the illustrated embodiment, the pyramidal polyhedron includes a regular triangular pyramid in which each of three base edges of the pyramid is defined by one of attached basal edges 42, and each of three side edges of the pyramid is defined by one of slits 50, and the side edges intersect at a vertex having a point within port axis P.

Figures 5, 6:
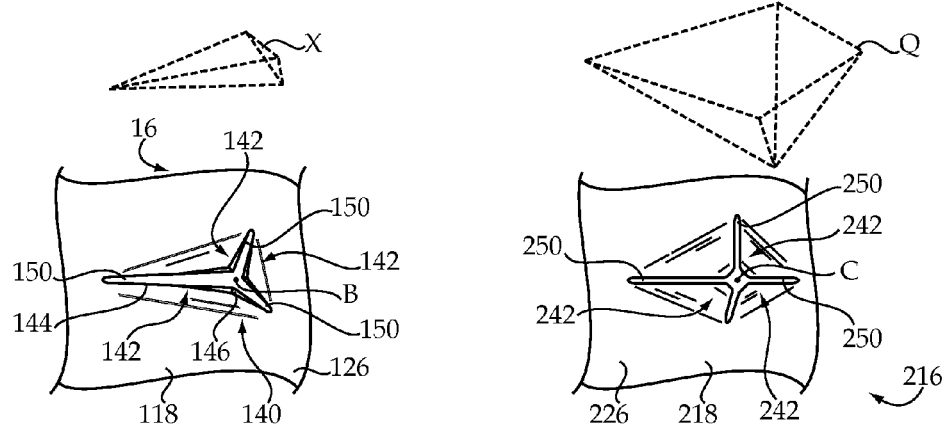
FIG. 5 is an elevational view of a portion of an infusion catheter, according to another embodiment.
FIG. 6 is an elevational view of a portion of an infusion catheter, according to yet another embodiment.

Turning now to FIG. 5, there is shown an infusion catheter 116 according to another embodiment, wherein a set of convergent leaves 142 formed integrally with material of an elongate catheter body 118 define a stellate side port 140 having a configuration different from that of the embodiment described above. In particular, stellate side port 140 has a configuration which might result from passing a piercing tool similar to tool 100 from an inside-to-outside direction, and at a non-perpendicular piercing angle, in contrast to the technique used to form side ports 40. Rather than leaves curving inwardly from an outer body surface, leaves 142 curve upwardly or outwardly relative to an outer body surface 126 of catheter body 118. Terminal tips 146 may thus be understood to point upwardly or outwardly rather than plunging inwardly as in the previously described embodiment. A set of three slits 150 are defined by leaves 142 and radiate outwardly from a center port axis B. It may be noted that slits 150 do not all have the same length, in particular slits 150 may include two approximately equal length slits having a relatively short radial length relative to axis B, and one longer radial length slit. Also illustrated in FIG. 5 is a pyramidal polyhedron shown in phantom lines and denoted via reference letter X. The pyramidal polyhedron X is defined by attached basal edges of leaves 142 and slits 150 similar to that of the pyramidal polyhedron discussed in connection with the foregoing embodiment. In contrast to side ports 40, polyhedron X may include a non-regular pyramid, and may project upwardly and away from outer body surface 126 toward a vertex which lies outside of catheter body 118.

Referring now to FIG. 6, there is shown an infusion catheter 216 according to yet another embodiment, and having a stellate side port 240 defined by a set of four convergent leaves 242 formed integrally with an elongate catheter body 218, and having four radiating slits 250 defines by leaves 242. Slits 250 may include four different radial lengths relative to a center port axis C, and are not radially symmetric about center port axis C. Stellate side port 240 might be formed by a piercing tool having an asymmetrically shaped tip which imparts the radially asymmetric pattern to leaves 242 and slits 250. To form side port 240, the piercing tool might be passed in an outside-to-inside direction at a piercing angle normal to the associated longitudinal axis of catheter body 218. Similar to stellate side ports 40 of infusion catheter 16, leaves 242 may plunge inwardly relative to an outer body surface 226 of catheter body 218. A polyhedron, approximately as might be defined by leaves 242 and slits 250 is shown in phantom lines in FIG. 6 and identified via reference letter Q. It may be noted that polyhedron Q may also be understood as a pyramidal polyhedron, but having a base which is a non-regular polygon, and four faces each having a different triangular shape and area.

INDUSTRIAL APPLICABILITY

Figure 7:
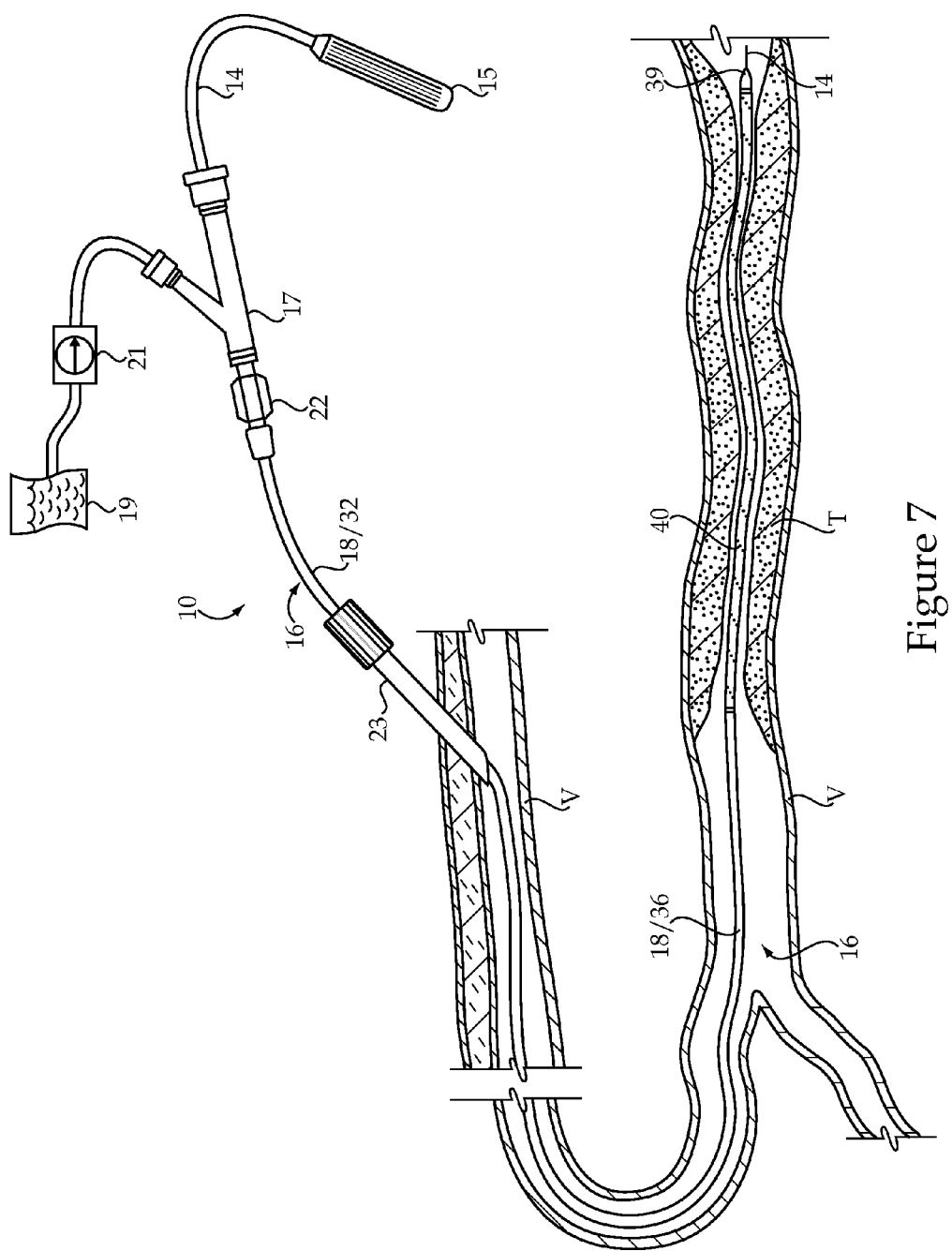
FIG. 7 is a pictorial view of an intraluminal treatment system at one stage of a treatment procedure, according to one embodiment.

Referring to the drawings generally but in particular to FIG. 7, there is shown intraluminal treatment system 10 as it might appear having been positioned for performance of an infusion procedure on a patient. Catheter 16 passes through an introducer 23 or the like and into a body lumen of a patient. The body lumen may include a vascular structure V such as a vein or artery. Catheter 16 is positioned such that distal segment 36 is located at a treatment site within vascular structure V, where a thrombus T has formed. Wire guide 14 passes through catheter body 18 and extends out through distal tip 39 via gated opening 60. Stellate side ports 40 provide fluid communication between an intraluminal space within vascular structure V and fluid supply passage 30 of catheter 16. A fitting 17 such as a Y-fitting is coupled with manifold 22 such that an infusion pump 21 can supply a treatment fluid such as a thrombolytic agent from an extraluminal fluid supply 19 into the body lumen of the patient.

A handle 15 is shown coupled with wire guide 14. It will be recalled that wire guide 14 may pass through gated opening 60 to enable guiding catheter 16 to a desired treatment location. For certain procedures, it may be desirable to withdraw wire guide 14 completely from infusion catheter 16, to optimize a flow area through passage 30 for delivering treatment agent to thrombus T. To this end, from the state shown in FIG. 7, wire guide 14 may be withdrawn from catheter 18 and the patient such that flaps 62 obstruct gated opening 60. Once wire guide 14 is withdrawn, or prior, pump 21 or another mechanism such as a pressure cuff may be activated to commence infusion. In a rapid-exchange version or an embodiment where a wire guide occlusion bulb obstructs an opening in a catheter tip, the wire guide might be left in place.

Figure 8:
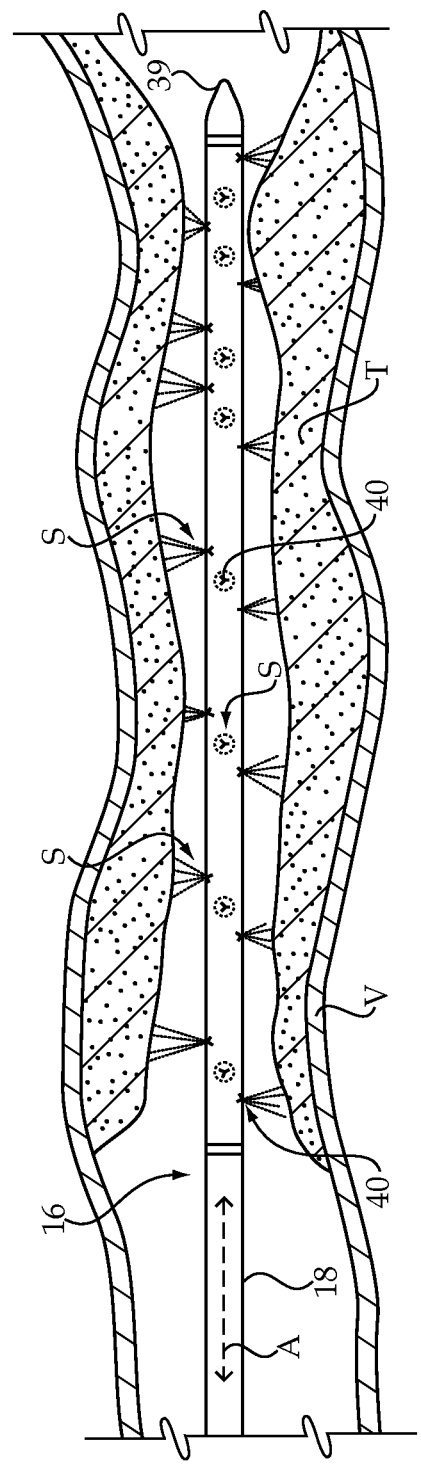
FIG. 8 is a pictorial view at another stage of the treatment procedure.

Referring also to FIG. 8, there is shown catheter 16 as it might appear having commenced infusion of a treatment fluid via stellate side ports 40. Infusion plumes S are shown in FIG. 8 illustrating an outward flow of treatment fluid from each of stellate side ports 40. Those skilled in the art will be familiar with the relative difficulty encountered in many conventional infusion procedures relating to achieving some degree of uniformity in flow of infusate from an infusion catheter. As treatment fluid is conveyed through an elongate catheter body, the treatment fluid tend to decrease in pressure. Stated another way, distal attenuation of infusion rate may tends to occur. In many conventional systems, distal attenuation of infusion rate may be so severe that little or no treatment fluid actually exits an infusion catheter in more distal regions of the catheter infusion length. The present disclosure improves substantially over many of these prior strategies. Passing treatment fluid through stellate side ports 40 may control infusion flow such that distal attenuation of an infusion rate is substantially reduced as compared to other known strategies. In other words, rather than infusion rate being very low or near zero in more distal portions of the catheter infusion length, flow rates may be closer to uniform over the entire catheter infusion length. This is believed to be due at least in part to a throttling effect of stellate side ports 40, and other side port configurations contemplated herein, on a flow of the treatment fluid. In addition, the non-uniform longitudinal distribution of stellate side ports in certain embodiments may further enhance the reduction in distal attenuation of infusion flow rate.

When treatment fluid is introduced into catheter 16, and conveyed to the infusion length thereof, it will typically lose some pressure. However, as treatment fluid fills passage 30 a pressure of the treatment fluid may be elevated due to the throttling effect of stellate side ports 40. In other words, rather than freely flowing out of side ports 40, some back pressure may be generated. Stellate side ports 40 may be initially in a rest state, but be adjusted to an activated state in response to elevating pressure within passage 30. The rest state may include a normally open state, but only slightly open such that flow is restricted or throttled, as shown in the attached drawings. The activated state may be a relatively more open state, assumed in response to elevating the pressure in passage 30, at which leaves 42 spread slightly to enlarge effective flow area through the associated side port 40. Once a pressure of the treatment fluid more or less equalizes throughout the entire catheter infusion length, infusion fluid may begin to flow out of all or substantially all of stellate side ports 40. In one practical implementation strategy, a closing bias of flaps 62 may be insensitive to elevating fluid pressure within fluid supply passage 30 to a point sufficient to achieve relatively uniform infusion. In other words, gated opening 60 may remain closed or nearly closed during the infusion procedure, as flaps 62 may have a closing bias which is sufficient to maintain opening 60 in a closed state despite elevating pressure within fluid supply passage 30.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, example catheter configurations are disclosed herein having certain dimensions and port arrangement patterns. In other embodiments, shorter or longer total catheter lengths, and different catheter infusion lengths might be used, such as a 20 cm or 70 cm catheter infusion length. Stellate side ports in a catheter having a relatively short infusion length might have a uniform density, whereas a catheter having a relatively long infusion length might include stellate side ports arranged such that their density continuously increases from a proximal end of the infusion length toward a distal end. Other aspects, features and advantages will be apparent upon an examination of the drawings and appended claims.

What is claimed is:

1. An infusion catheter comprising:
    an elongate catheter body including an outer body surface, and an inner body surface defining a fluid supply passage extending longitudinally between a proximal body segment having an inlet to the fluid supply passage, and a distal body segment;
    a plurality of stellate side ports in fluid communication with the fluid supply passage and having a distribution within the distal body segment which defines a catheter infusion length;
    each of the stellate side ports being defined by sets of at least three convergent leaves formed integrally with the elongate catheter body, and each of the convergent leaves having an attached basal edge, a terminal tip, and first and second free edges extending between the attached basal edge and the terminal tip;
    the distal body segment terminating in a wire guide opening; and
    wherein the infusion catheter has an infusion configuration in which the stellate side ports are open to fluid flow therethrough and the wire guide opening is obstructed to fluid flow therethrough.

2. The infusion catheter of claim 1 wherein each of the stellate side ports includes slits radiating outward from a center port axis, and each of the convergent leaves adjoins two of the slits and includes a taper narrowing toward the corresponding center port axis.

3. The infusion catheter of claim 2 wherein the stellate side ports are open in a rest state.

4. The infusion catheter of claim 2 wherein each of the stellate side ports is radially symmetric and axially asymmetric.

5. The infusion catheter of claim 4 wherein:
    each of the convergent leaves defines a triangular shape in a projection plane intersecting and oriented normal to the corresponding center port axis, and curves inwardly from the outer body surface such that the terminal tip is incident to an outward flow of fluid from the fluid supply passage; and
    each of the convergent leaves defines a curve in a section plane which includes a plane of the corresponding center port axis, and the curve having a shallower incipient segment and a steeper terminal segment.

6. The infusion catheter of claim 2 wherein the attached basal edge of each one of the convergent leaves defines one edge of a pyramidal polyhedron, and wherein each of the adjoining slits defines one edge of the corresponding pyramidal polyhedron.

7. The infusion catheter of claim 6 wherein a number of the stellate side ports is equal to ten or greater, and wherein the stellate side ports are positioned at a plurality of different radial locations about a longitudinal center axis of the fluid supply passage.

8. The infusion catheter of claim 7 wherein the distal body segment includes a distal tip, and the wire guide opening is a gated wire guide opening formed in the distal tip and communicating with the fluid supply passage, and a plurality of deformable flaps configured to open and close the gated wire guide opening in response to inserting and removing a wire guide through the gated wire guide opening, respectively.

9. A method of making an infusion catheter comprising the steps of:
    forming a plurality of stellate side ports in fluid communication with a fluid supply passage in an elongate catheter body, each of the stellate side ports being defined by a set of at least three convergent leaves; and
    setting an infusion length of the infusion catheter during the forming step at least in part by spacing the stellate side ports longitudinally between proximal and distal ends of the elongate catheter body.

10. The method of claim 9 wherein the step of forming further includes simultaneously cutting the convergent leaves of each set from material of the elongate catheter body.

11. The method of claim 10 wherein the step of forming further includes forming each of the stellate side ports without removing the material of the elongate catheter body.

12. The method of claim 10 wherein cutting the convergent leaves further includes passing a pyramidal tip of a piercing tool through a body wall of the elongate catheter body.

13. The method of claim 12 wherein cutting the convergent leaves further includes stopping the pyramidal tip at a partial insertion depth within the body wall, and withdrawing the piercing tool from the partial insertion depth.

14. The method of claim 9 further including a step of forming a gated opening in the distal end of the elongate catheter body, for passing the infusion catheter over a wire guide.

15. A method of supplying a treatment fluid into a body lumen of a patient comprising the steps of:
    conveying treatment fluid through a longitudinally extending fluid supply passage in an elongate catheter body of an infusion catheter;
    infusing the treatment fluid from the elongate catheter body into the body lumen; and
    controlling an infusion flow of the treatment fluid at least in part by obstructing a wire guide opening trough a distal tip of the infusion catheter and passing the treatment fluid through a plurality of stellate side ports defined by sets of at least three convergent leaves and fluidly connecting the fluid supply passage with the body lumen.

16. The method of claim 15 wherein the step of controlling further includes limiting distal attenuation of an infusion rate via throttling a flow of the treatment fluid with the stellate side ports.

17. The method of claim 16 wherein the step of controlling further includes limiting the distal attenuation via a non-uniform longitudinal distribution pattern of the stellate side ports.

18. The method of claim 16 wherein passing the treatment fluid further includes passing the treatment fluid through at least three radiating slits of each one of the stellate side ports.

19. The method of claim 18 wherein passing the treatment fluid further includes passing the treatment fluid about sets of at least three convergent leaves defining each of the stellate side ports and having terminal leaf tips positioned incident to a flow of the treatment fluid.

20. The method of claim 16 further comprising the steps of positioning the infusion catheter at a treatment location within the body lumen at least in part by sliding the elongate catheter body over a wire guide passing through a distal opening to the fluid supply passage, and then removing the wire guide from the opening.

21. The method of claim 20 further comprising the steps of elevating fluid pressure within the fluid supply passage in response to throttling the flow of treatment fluid, and blocking the opening after removing the wire guide by way of a plurality of deformable flaps having a closing bias which is insensitive to the elevated fluid pressure.

* * * * *